United States Patent [19]
Downie et al.

[11] 4,454,643
[45] Jun. 19, 1984

[54] COMBINATION MEMBRANING TOOL, PACKAGE AND CALIBRATION UNIT FOR EYELID SENSOR OR THE LIKE

[75] Inventors: David E. Downie, Lafayette; Gary Schneiderman; Eric D. Shulse, both of Walnut Creek; Stanley J. Withers, Oakland, all of Calif.

[73] Assignee: Thoratec Laboratories Corporation, Berkeley, Calif.

[21] Appl. No.: 255,682

[22] Filed: Apr. 20, 1981

[51] Int. Cl.³ .............................................. B25B 27/14
[52] U.S. Cl. ................................................... 29/270
[58] Field of Search ......................... 73/16, 29, 343 B; 53/488, 139.3, 297; 206/5.1, 305, 210, 212, 205; 29/270, 271, 272, 281.1, 281.5, 251

[56] References Cited
U.S. PATENT DOCUMENTS

| | | | |
|---|---|---|---|
| 936,893 | 10/1909 | Hicks | 53/488 |
| 2,454,602 | 11/1948 | Gunther | 206/210 |
| 3,460,951 | 8/1969 | Heyl | 53/488 |
| 3,769,961 | 11/1973 | Fatt et al. | 128/635 |
| 3,977,517 | 8/1976 | Kadlecik et al. | 206/5.1 |
| 4,228,136 | 10/1980 | Thomas | 206/5.1 |

*Primary Examiner*—Robert C. Watson
*Attorney, Agent, or Firm*—Flehr, Hohbach, Test, Albritton & Herbert

[57] ABSTRACT

A tool for applying a membrane on a small upstanding post like device, which tool incorporates a housing with means for securing the membrane across the top of the post with additional means disposed opposite the post for holding the membrane against the post and urging it down the side of the post, the housing being closeable to serve as a shipping container and a calibration cell for the device to be membraned with means to secure the post captive with little or no chance of its falling into a non-sterile environment.

10 Claims, 11 Drawing Figures

COMBINATION MEMBRANING TOOL, PACKAGE AND CALIBRATION UNIT FOR EYELID SENSOR OR THE LIKE

The present invention is directed to a tool and method for applying membranes to small upstanding post like devices in such a manner that the membrane will remain smooth and completely extended over the surface of the upstanding post like structure. The tool also forms a shipping package for the device to be membraned and, when that device includes a detector, the tool and package may also serve as a calibration unit.

In the manufacture or preparation of various devices it is frequently necessary that a relatively small membrane be fitted over a post like structure having a diameter of perhaps ⅛ of an inch or less. One such device which may require the application of such small membranes is a conjunctival device of the general type as shown in U.S. Pat. No. 3,769,961—something known broadly as an eyelid sensor. In such a device one or more detectors is disposed on the surface of a carrier adapted to be positioned between the sclera and the palpebral conjunctiva so as to provide noninvasive measurement of the partial pressure of oxygen or the like. The detector may include a post like structure which requires a membrane of particular character to be positioned across its surface for contact with the palpebral conjunctiva when the device is employed for use on a patient or subject. Moreover, between the membrane and the post like structure it is often required that a fluid be added at the time of use of the device. Consequently, the application of the membrane must be done by the user as such or the attending physician rather than at an assembly plant where conventional tooling for such assembly would be economically feasible. It is, therefore, necessary to provide means to apply the membrane manually with sufficient accuracy to insure that the membrane is properly positioned over the post like device; that it covers the entire top of the post like device which is to be in contact with the conjunctiva and that the membrane is not torn or otherwise breached by the application procedure itself. Moreover, even though the membrane for an eyelid sensor is to be applied by the user, the membrane, as well as the carrier for the sensor may have to be kept clean or sterile not only during shipment but also during the membraning operation and while the unit is being calibrated if such calibration is required.

It is an object of this invention to provide an improved membrane application tool and method for applying such membranes in a non-manufacturing environment.

It is also an object to provide such a tool which may also serve as a packaging unit and calibration cell so as to keep sterile the device being membraned.

In accordance with these objects there is provided an apparatus for applying a membrane which apparatus incorporates a housing including within it means for securing a post across the top of which the membrane is to be applied. Additional means is disposed opposite the post for securing the membrane temporarily, and for holding its center against the post while simultaneously urging its periphery down about the sides of the post. Means is also provided to install a keeper ring so as to maintain the membrane in position. The membrane is thus not only held tightly across the top of the post but is assured to extend all the way across the top of the post and not to be moved off center during application and subsequent use. The entire tool may be used as a shipping container for the device to be membraned. The means for securing the post may well include means for holding captive a carrier for the post such that there will be little or no chance of its falling into a non-sterile environment during shipping or during the membraning operation itself. The tool may also be closeable about the sensor so as to form a cell for calibration of the membraned device in the proper calibration environment, such environment sometimes requiring heat and temperature control.

Referring to the drawing FIG. 1 is a cross section on an axial plane through an assembly fixture for lodging a membrane onto a sensor cell in an eyelid sensor carrier in accordance with one embodiment of the invention.

Very often it is highly desirable to detect various factors present in the human body by establishing a detecting mechanism in contact with the palpebral conjunctiva on the inner surface of the eyelid, particularly the upper eyelid. This is highly advantageous since in that unique portion of the body there are very few obstructing intervening cells between the interior mechanism of the body and the conjunctiva surface itself.

An arrangement of this general character is shown in U.S. Pat. No. 3,769,961, issued Nov. 6, 1973 to Fatt and Kitrilakis. In devices of the nature shown in said patent as well as in improvements thereover it is frequently necessary that a miniature detector or sensor installed in a relatively small carrier be prepared or conditioned for use by the user prior to its placement adjacent to the conjunctiva. Such conditioning may require the application of a fluid over the sensor itself and a membrane about the fluid and the sensor. The type of fluid as well as the type of membrane may vary considerably depending upon the type of sensing activity to be undertaken.

Figure 1:
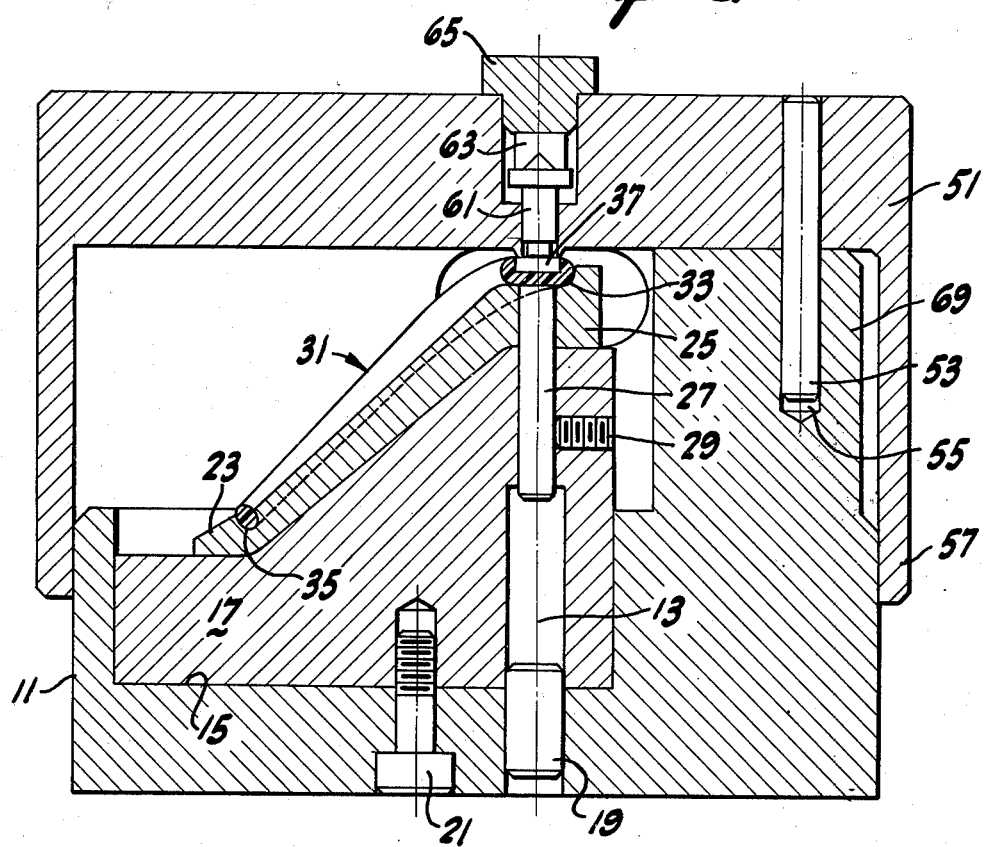
Figure 2:
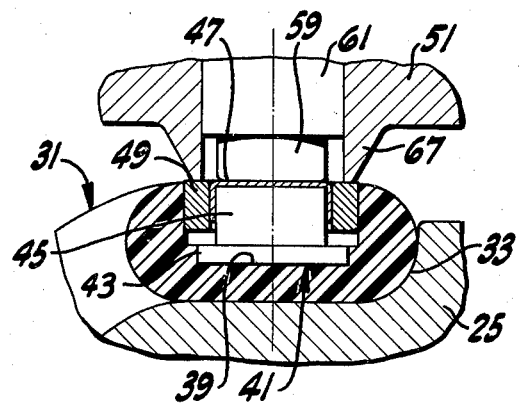
FIG. 2 is an enlarged detail of a portion of the fixture and sensor cell shown in FIG. 1.

In order to apply such a membrane, as well as to change and wet it from time to time, there is provided, as shown in FIGS. 1 and 2, a tool for assisting in this operation. A base 11 has a vertical axis 13 and is formed with an eccentric opening 15 receiving a circular plug 17 located on the axis 13 by a pin 19. The plug 17 is removably held in place by a fastening screw 21 so that the plug can be changed from time to time. The plug is designed to removably carry a changeable adaptor 23. The adapter has a hub 25 resting against and aligned with the plug 17 by an axial pin 27 fixed by a screw 29. The adaptor 23 can readily be changed or replaced by other adaptors, each especially shaped and sized for particular eyelid sensor carriers such as 31. Each adaptor has a head recess 33 and a toe recess 35 precisely located to receive specific ones of a group or family of carriers. The head recess 33 is formed accurately to position coaxially and firmly the part of the carrier in which the body of the detector shown schematically at 37 is formed, while the recess 35 carries the opposite end of the carrier.

The carrier 31 to be operated upon is positioned on the adaptor 23. The recesses 33 and 35 together act to hold the sensor carrier captive so that a positive pull on the carrier is required to cause its release. Located in a chamber 39 (see FIG. 2) of the carrier is a detector body 41 having a base flange 43 fitting the bore of the chamber 39 and having a central post like boss or stud 45. When a membrane is to be applied a drop of solution such as electrolyte is placed on top of the boss, and a membrane 47 is positioned on the solution drop. A keeper ring 49 carried on a cover cup 51 is urged down over the membrane disc and electrolyte onto the boss 45.

The cover cup 51 has a locating pin 53 extending down into a bore 55 in the base 11. The cup 51 also includes a skirt-like flange 57 in sliding engagement with the base 11.

The cover 51 is moved downwardly until the reduced lower base 59 (see FIG. 2) of a plunger or pin 61 contacts the membrane 47. Alternatively, the membrane 47 may have been temporarily affixed to and carried by the lower base 59 and in such instance, the cover 51 is moved downward until the membrane 47 is positioned on the boss 45. As the cover 51 continues its downward movement, the lower base 59 holds the membrane in contact with the boss 45 but its downward movement is discontinued. The cover 51, on the other hand, continues downward movement resulting in compression of a sponge 63 confined by a plug 65. As the cover continues to descend a conical rim 67, resting on the ring 49, forces that ring downwardly about the boss 45 and the peripheral portion of the membrane 47 is folded down the sides of the boss. The downward movement of the cup 51, rim 67 and keeper ring 49 continues until the bottom of the ring almost contacts the flange 43. At this point the cover 51 abuts the upstanding block 69 forming a part of the base 11. Thereafter the cover 51 is lifted away and the carrier 31 is removed from the fixture ready for calibration and use.

The membraning tool as shown in FIG. 1 is adequate, accurate and suitable for reuse, particularly in a laboratory environment. Frequently, however, the use of such conjunctival sensors are required at locations where membraning devices such as shown in FIGS. 1 and 2 will not be practical. To accommodate such needs a less expensive, disposable and more portable membraning tool is provided as shown in FIGS. 3 through 9.

In the apparatus of FIGS. 3 through 9 there is shown a base member 101 having side walls 103 and 105 and end walls 107 and 109, as well as two spaced intermediate walls 111 and 113. A tray 115 is disposed on the base 101, said tray including a receptacle portion 117 and a cover portion 119 joined together by a hinge portion 121. The receptacle portion 117 is generally bowl shaped but is preformed to include a somewhat resilient deformation 123 shaped as a recess to receive a device such as the eyelid sensor carrier 125. The resiliency at the deformation is sufficiently strong that the carrier 125 is held captive in the deformation 123 and will not fall out during shipping and handling. It may, however, be easily withdrawn by hand.

The cover portion 119 includes a tab 127 which may be used to flip the cover about the hinge 121 so as to close the top of the receptacle portion 117. The cover portion includes, as viewed from FIG. 4, a raised portion 129 which is adapted to fit within the receptacle portion 117 for alignment therewith. Such alignment can, for instance, be accomplished by accurately positioning the walls of the receptacle 117 and raised portion 129 of the cover 119. In addition, the cover carries an insert 131 and pin 133, seen in greater detail in FIG. 5. The pin 133 fits in a corresponding opening of the insert 131 by frictional engagement and a keeper ring 135 is carried on the pin, also by frictional engagement. A membrane disc 137 is carried on top of the pin 133 and held there by a low strength adhesive for relatively easy separation during assembly. The adhesive should have a greater affinity to the material of the pin than it does to the membrane itself. The adhesive must also be bio-compatible and is ideally soluble in the electrolyte or other fluid used so that any remnant on the membrane, if any, may be easily rinsed away. A seven percent (7%) solution of polyvinyl alcohol in distilled water has been found to be effective as such an adhesive when the pin 133 is formed of polymethylmethacrylate (PMMA) and the membrane is formed of polypropylene. Different adhesives may be required to satisfy this parameter when the membrane is formed of other material such as polyethelene, Teflon or silicon rubber and/or if the pin if formed of a different material.

Figure 3:
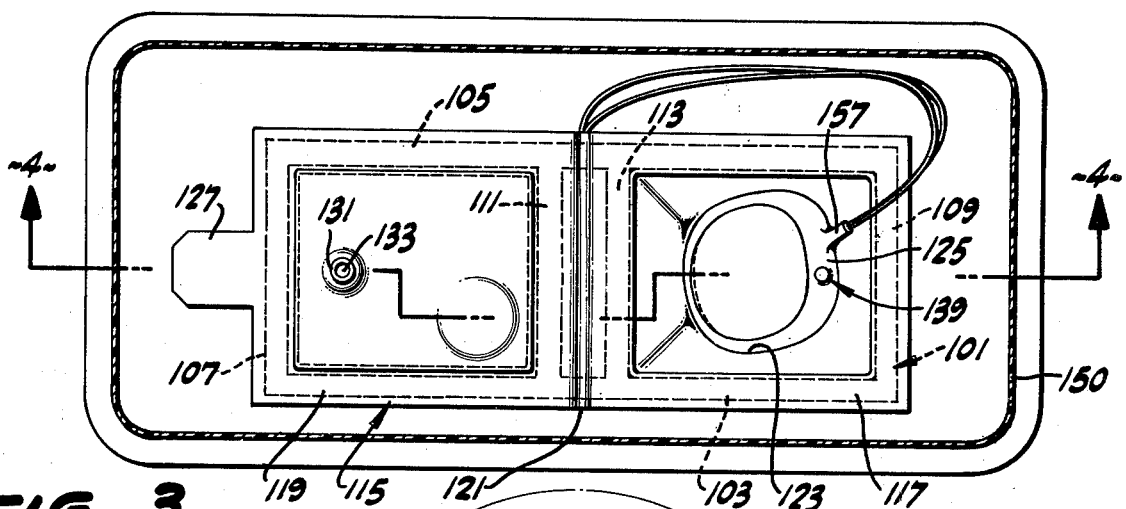
FIG. 3 is a top plan view of a preferred form of portable assembling fixture for lodging a membrane onto a sensor cell in an eyelid sensor carrier.
Figure 4:
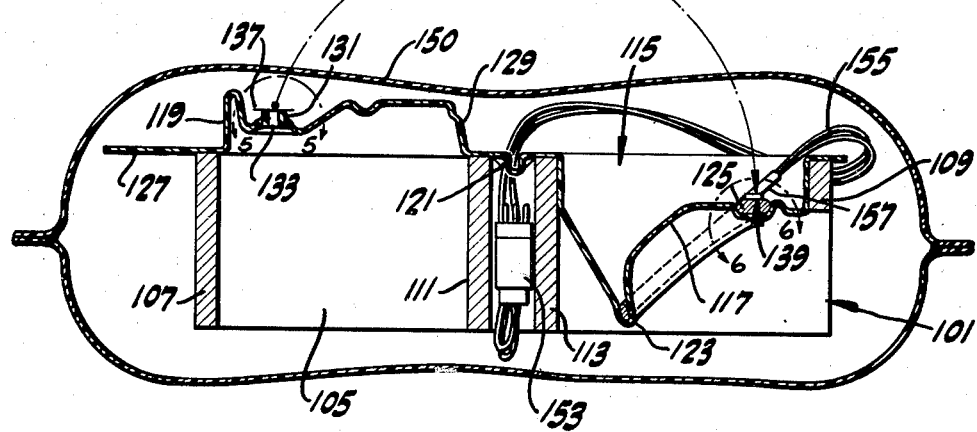
FIG. 4 is an elevational section view taken along the line 4—4 of FIG. 3.
Figure 5:
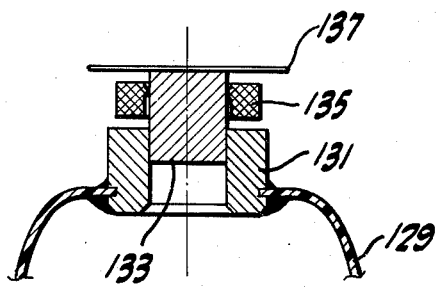
FIG. 5 is an enlarged detail view taken along the line 5—5 of FIG. 4.
Figure 6:
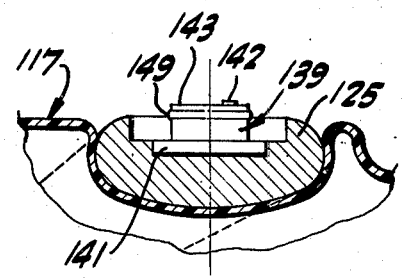
FIG. 6 is an enlarged detail view taken along the line 6—6 of FIG. 4.

The carrier 125 includes a detector body 139, shown in greater detail in FIG. 6. The detector body may include a base flange 141 and a sensing element 142 positioned on top of a central boss 143. The arrangement is similar to, but shown in more detail than, that of FIGS. 1 and 2. The deformation 123 in the receptacle portion 117 is located so as to accurately position the carrier 125 in a manner generally as shown in FIGS. 3 and 4. The insert 131 is likewise accurately positioned but on the cover portion 119. The position of the insert 131 is such that as the cover 119 is swung about the hinge 121 and closed upon the receptacle portion 117, the insert 131 and pin 133 are aligned with post 143 of the cell body 139. Moreover, the upward extent of the insert 131 and 133, as seen in FIG. 4, is such that when the cover 119 is closed onto the receptacle portion 117 the insert 131 may extend to and lie over the boss 143 as will be seen hereinafter.

The entire assembly, as shown in FIGS. 3 and 4, can be conveniently packaged in a sterile pouch 150. In order to ready the eyelid sensor carrier for use the pouch merely need be opened avoiding contact with the tray portion 115 so as to maintain sterility. An electrolyte 144, a container of which may be included in the sterile package, can be removed and a small drop applied to the surface of the sensor at the top of the boss 143 and sensing element 142, just large enough to cover the entire surface.

Figure 7:
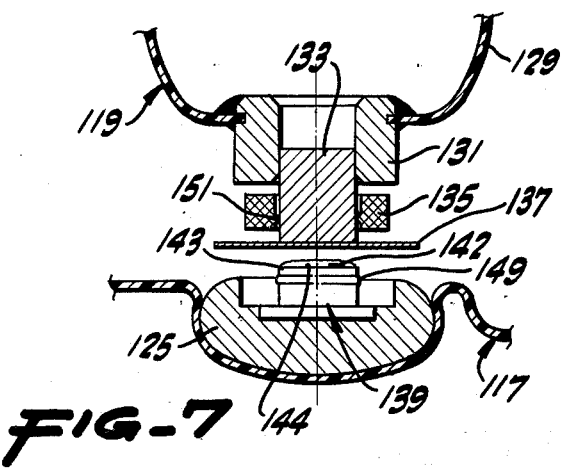
FIG. 7 is a diagrammatic view showing the portions of FIGS. 5 and 6 as the membrane is about to be affixed onto the sensor.
Figure 8:
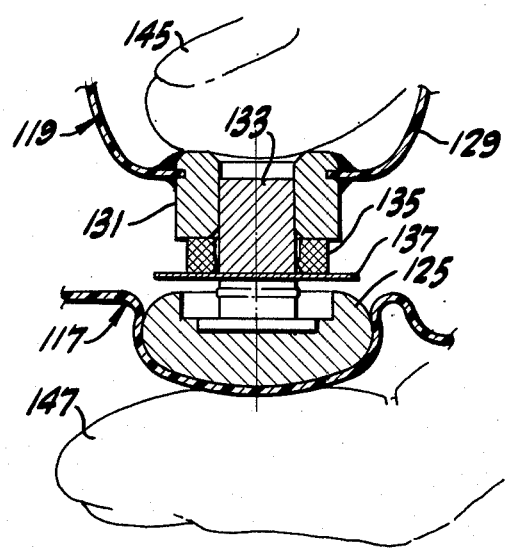
FIG. 8 is a view similar to FIG. 7 but showing the membrane positioned atop the sensor prior to being enveloped thereabout.
Figure 9:
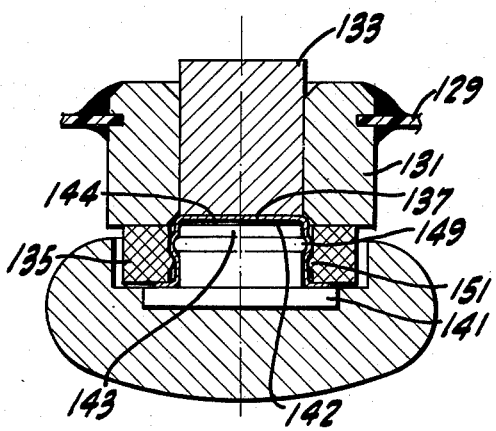
FIG. 9 is a view similar to FIGS. 7 and 8 but showing the membrane fully assembled on the sensor and with the plunger not yet removed.

Referring now specifically to FIGS. 7, 8 and 9, the use of the device shown in FIGS. 3 through 6 as a membraning tool will be understood. After applying the electrolyte 144 the tab 127 is used to swing the lid 119 about the hinge 121 to bring the parts into the position shown generally in FIG. 7 with the membrane 137 immediately above and concentric with the boss 143. After the parts reach the position as shown in FIG. 7 they may be urged closer together and in contact such as is shown in FIG. 8, by exertion of digital pressure between the thumb 145 and forefinger 147 of the assembler. In this position it can be seen that the pin 133 has been moved despite its frictional engagement with the insert 131 so that it slides upward in the insert. Moreover, the bottom of the insert contacts the keeper ring 135 and the keeper ring 135 is, in turn, urged downward relative to the pin such that it contacts the membrane disc 137. Upon even further digital pressure the parts take on the position as shown in FIG. 9 wherein the pin slides even further upward against its frictional engagement in the insert 131 and the bottom of the insert forces the keeper ring 135 completely off the pin 133 and onto the boss 143 in such a manner that it carries with it the peripheral portion of the membrane disc 137 to surround the upstanding sides of the boss and the captured layer of electrolyte 144. As can be seen particularly in FIG. 9 the boss may include an external annular rib 149 and the keeper ring 135 may include a corresponding internal annular rib 151 which, when in the position shown in FIGS. 5, 7, and 8, remains substantially compressed. However, when the keeper ring is positioned on the boss 143, the ribs 151 and 149 cooperate to maintain the keeper ring 135 in position. Moreover, it should be noted that during the entire time that the insert 131 is urging the keeper ring 135 and the membrane 137 downward, the pin 133, by its location, maintains the membrane 137 in centralized position on top of the boss 143. The various changes in position cannot, of course, be seen because the parts are held between and positioned by the user's fingers. Even so the assembled position can be detected by recognizing a slight snap as the keeper ring 35 moves into final position. Again using the tab 127 the lid may then be lifted and the top of the membrane washed with a remaining portion of the electrolyte removing any remnants of the adhesive. Additional electrolyte or other aqueous fluid may be placed in the receptacle portion 117, the lid may then be closed and the tray portion 115 removed from the base 101 so as to provide a humidified chamber which, if necessary, may be heated and serve as a calibration cell for the sensor. As is shown particularly in FIGS. 3 and 4 a connector 153 may be coupled to the carrier 125 by means of a wire 155 and a terminal body 157. The connector, of course, serves not only with respect to calibration but also with actual operation of the sensor in use.

The entire device as shown in FIGS. 3 through 9 can be made of relatively inexpensive materials. The base member 101 could even be formed of pasteboard while the tray portion 115 is conveniently made of vacuum formed plastic.

Figure 10:
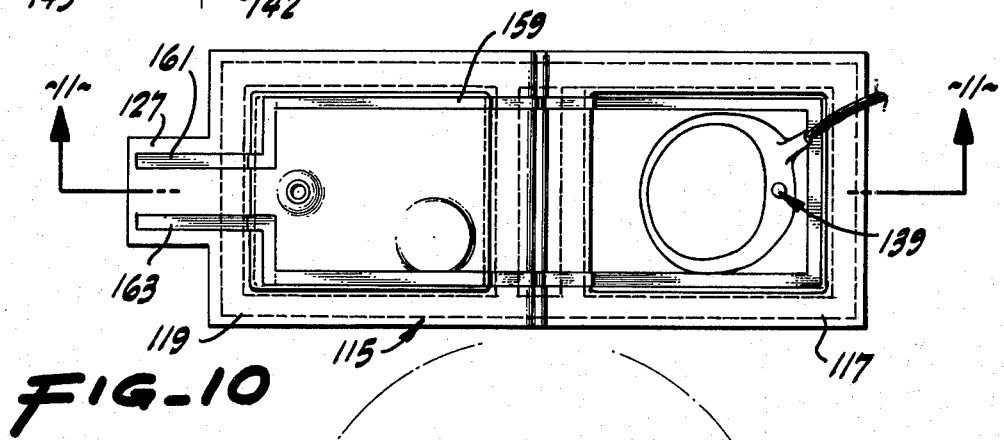
FIG. 10 is a view similar to FIG. 3 but of another form of another embodiment wherein the assembling fixture includes an integral heating element.
Figure 11:
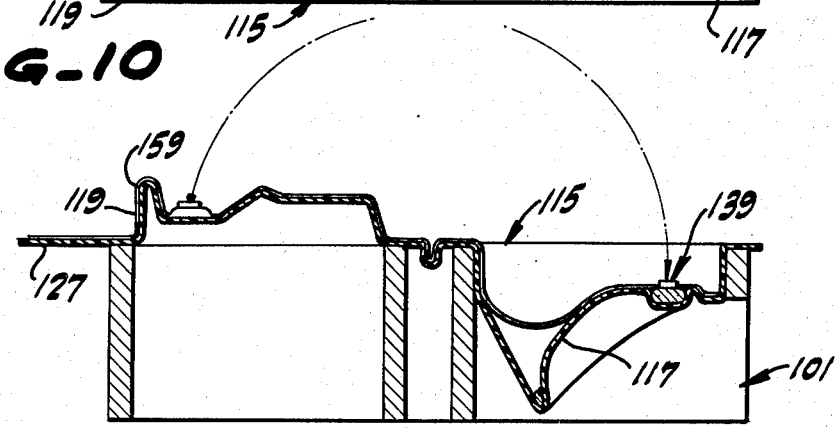
FIG. 11 is an elevational section view taken along line 11 of FIG. 10.

When used as a calibration chamber for the prepared detector it is often required that the temperature of the calibration fluid (e.g. gas) be controlled. This may, of course, be provided by placing the calibration chamber in or in contact with, a separate heater/controller. Alternatively, a heating element for this purpose may be incorporated in the tray portion 115 itself as shown in FIGS. 10 and 11. To this end the heating element may include a single run of a resistance heater 159 having ends 161 and 163 affixed to the tab 127. The run may be secured by conventional means to the surface of both the cover portion 119 and the receptacle portion 117. Preferably, the heater 159 passes near to the position of the detector body 139 so that sufficient heat may be supplied when it is needed. For this later application (i.e. heating with means integral to the tray) a temperature sensor is needed to allow temperature control. If the membraned detector itself also incorporates a temperature sensor, it may be used for this purpose; otherwise a separate temperature detector must also be incorporated within the tray along with the integral heating element.

What is claimed is:

1. Apparatus for applying a membrane across the end of a stud comprising a receptacle including a seat for receiving and holding the stud in a fixed position, a cover disposed for movement toward and away from said seat, said cover defining an opening alignment with said seat, the portion of said cover surrounding said opening defining ring engaging and pushing means, a pin disposed in and extending out of said opening, means for yieldingly restraining said pin in said opening against axial movement, said pin having a cross section substantially the same as that of the stud and being adapted to receive and frictionally engage a keeper ring about that portion thereof extending out of said opening, and means for urging said cover toward said seat until the movement of said pin is arrested by the stud in the seat such that it is forced further into said opening overcoming said means for yieldingly restraining said pin and the keeper ring is forced off the pin and onto the stud by the continued movement of the cover thereby positioning and capturing the membrane about the stud.

2. Apparatus as defined in claim 1 together with a hinge joining said receptacle and said cover.

3. Apparatus as defined in claim 1 wherein said pin is frictionally engaged in said opening.

4. Apparatus as defined in claim 1 wherein said pin is resiliently restrained against axial movement.

5. A portable membraning tool for preparing a carrier with a detector requiring a membrane, said tool comprising, a tray said tray including a receptacle member a cover member and a hinge portion interconnecting said receptacle and cover members whereby said tray can be changed from a first position with both the receptacle and the cover member facing upward to a second position with the cover overlying and facing downward onto said receptacle said receptacle member being generally bowl shaped and including means for releasably securing the carrier with the detector extending generally upward, said cover member including a sleeve, a pin frictionally engaged in said sleeve and extending upwardly therefrom when said tray is in its first position, a keeper ring frictionally disposed about that portion of the pin extending from the sleeve, a membrane disc lightly adhered to the end of the pin extending from the sleeve, said pin being positioned on the cover member corresponding to the position of the detector in said receptacle member, said cover and receptacle members each including means for applying digital pressure to force them together when the tray is in its second position whereby the membrane is held by the pin tightly against the face of the detector body and upon an increase in pressure the pin is forced into the sleeve and the end of the sleeve forces the periphery of the membrane disc and the keeper ring down and about the detector body.

6. A portable membraning tool as defined in claim 5, together with an adhesive lightly adhering said membrane disc to said pin, said adhesive having a greater affinity for said pin than for said membrane disc.

7. A portable membraning tool as defined in claim 5 wherein said membrane disc is formed of polypropylene and said pin is formed of polymethylmethacrylate, said membrane disc being lightly adhered to said pin by a solution of polyvinyl alcohol in water.

8. A portable membraning tool for preparing a carrier having a detector body with a detector requiring a membrane, said tool comprising a receptacle member, a cover member disposed opposite said receptacle member, said receptacle member including means for releasably securing the carrier with the detector extending toward said cover, said cover member including a sleeve, a pin disposed in and extending out of said sleeve and yieldingly restrained therein against axial movement, a keeper ring frictionally disposed about that portion of the pin extending from the sleeve, a membrane disc lightly adhered to the end of the pin extending from the sleeve, said pin being positioned on said cover member in alignment with the detector on said receptacle member, said cover and receptacle member each including means for applying digital pressure to force them together whereby upon application of pressure the membrane is held by the pin tightly against the face of the detector body and upon an increase in pressure the pin is forced into the sleeve and the end of the sleeve forces the periphery of the membrane disc and the keeper ring about the detector body.

9. A portable membraning tool as defined in claim 8 wherein one of said members is generally bowl shaped whereby a humidifying fluid may be carried thereby.

10. A portable membraning tool as defined in claims 5 or 8 together with temperature control means secured to at least one of said members.

* * * * *